(12) United States Patent
Wilson et al.

(10) Patent No.: US 10,886,018 B2
(45) Date of Patent: Jan. 5, 2021

(54) DYNAMIC AND MIXED RENDERING MECHANISMS FOR MEDICAL IMAGES

(71) Applicant: INTERNATIONAL BUSINESS MACHINES CORPORATION, Armonk, NY (US)

(72) Inventors: Terence Wilson, Newmarket (CA); Jie Pei, Mississauga (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 365 days.

(21) Appl. No.: 15/944,293

(22) Filed: Apr. 3, 2018

(65) Prior Publication Data
US 2019/0304590 A1    Oct. 3, 2019

(51) Int. Cl.
| | | |
|---|---|---|
| *G16H 30/20* | (2018.01) | |
| *G16H 30/40* | (2018.01) | |
| *G16H 80/00* | (2018.01) | |
| *G06T 7/00* | (2017.01) | |
| *G16H 50/20* | (2018.01) | |
| *G16H 15/00* | (2018.01) | |
| *G16H 10/60* | (2018.01) | |

(52) U.S. Cl.
CPC .......... *G16H 30/20* (2018.01); *G06T 7/0012* (2013.01); *G16H 30/40* (2018.01); *G16H 80/00* (2018.01); *G06T 2207/30004* (2013.01); *G16H 10/60* (2018.01); *G16H 15/00* (2018.01); *G16H 50/20* (2018.01)

(58) Field of Classification Search
CPC ........ G16H 30/20; G16H 30/40; G16H 80/00; G16H 50/20; G16H 15/00; G16H 10/60; G16H 40/20; G16H 40/63; G06T 7/0012; G06T 2207/30004
See application file for complete search history.

(56) References Cited

U.S. PATENT DOCUMENTS

| | | | | |
|---|---|---|---|---|
| 2013/0321456 A1* | 12/2013 | Hultquist | ................. | G09G 5/14 345/629 |
| 2014/0029615 A1* | 1/2014 | Baldwin | ............. | H04L 67/2828 370/392 |
| 2015/0154778 A1* | 6/2015 | Hughes | ................. | G06F 19/321 345/629 |

(Continued)

Primary Examiner — Qian Yang
(74) Attorney, Agent, or Firm — Michael Best & Friedrich LLP

(57) ABSTRACT

Methods and systems for providing dynamic and mixed rendering of medical images on a client device. The client device receives user input selecting a medical image and determines whether system capabilities of the client device satisfy conditions for performing client-side rendering of the medical image. In response to determining that the system capabilities satisfy the conditions for performing client-side rendering, the client device retrieves raw image data corresponding to the medical image from an image repository and provides the data to the image viewer application for client-side rendering of the medical image within the image viewer application. In response to determining that the system capabilities do not satisfy the conditions for performing client-side rendering of the medical image, the client device provides a server-side rendered version of the raw medical image data corresponding to the medical to the image viewer.

18 Claims, 5 Drawing Sheets

(56) References Cited

U.S. PATENT DOCUMENTS

2015/0320365 A1* 11/2015 Schulze ................ A61B 5/748
                                                                           600/408
2019/0199803 A1*  6/2019 Murray ................. H04L 67/08

* cited by examiner

DYNAMIC AND MIXED RENDERING MECHANISMS FOR MEDICAL IMAGES

FIELD

Embodiments described herein relate to image viewers and, in particular, image viewers for viewing medical images and automatically determining how to render medical images within the viewers based on capability of the user device executing the image viewer.

SUMMARY

Medical images collected as part of medical studies are stored in an image repository. A medical professional can access and view these medical studies at a remote device using a browser application or a dedicated viewer application.

A viewer application may use server-side image rendering. When using server-side image rendering, a server, which controls access to the image repository, converts raw medical image data (stored, for example, in a DICOM format, Nifti format, or the like) stored on the image repository to an image file (for example, in JPEG, PNG, or other image or video formats). The server then sends the image file to the remote device for display to a requesting user. When a user subsequently requests a modification of the image (for example, changing a level of magnification, adding measurements, or the like), the remote device sends a request to the server, and the server performs the requested modification on the raw medical image data and converts the modified data to a second image. The server then sends the second image to the remote device for display to the user. Server-side rendering may be fast and effective when the remote device and the server are located at the same entity (for example, at the same hospital, clinic, or other facility). However, in other situations, server-side rendering may cause slow loading of images, such as when the remote device and the server are communicating over a slow Internet connection.

Accordingly, embodiments described here provide systems and methods for providing dynamic and mixed rendering mechanisms for medical images. For example, one embodiment provides a method that includes receiving user input selecting a medical image for display within an image viewer application executed by the client device and determining system capabilities of the client device. The method also includes determining, with an electronic processor, whether the system capabilities of the client device satisfy conditions for performing client-side rendering of the medical image. In response to determining that the system capabilities of the client device satisfy the conditions for performing client-side rendering of the medical image, the method includes retrieving raw medical image data corresponding to the medical image from an image repository and providing the raw medical image data corresponding to the medical image to the image viewer application executed by the client for client-side rendering of the medical image within the image viewer application. In response to determining that the system capabilities of the client device do not satisfy the conditions for performing client-side rendering of the medical image, the method includes providing a server-side rendered version of the raw medical image data corresponding to the medical to the image viewer.

Another embodiment provides a system including an electronic processor configured to receive user input selecting a medical image for display within an image viewer application executed by the client device. The medical image includes image data and overlay data defining an overlay for the image data. The electronic processor is also configured to determine system capabilities of the client device and determine for the image data included in the medical image, whether the system capabilities of the client device satisfy conditions for performing client-side rendering of the image data. In response to determining that the system capabilities of the client device satisfy the conditions for performing client-side rendering of the image data, the electronic processor is further configured to retrieve the image data and the overlay data and provide the image data and the overlay data to the image viewer application for client-side rendering of the image data and the overlay data within the image viewer application. In response to determining that the system capabilities of the client device do not satisfy the conditions for performing client-side rendering of the image data, the electronic processor is further configured to provide a server-side rendered version of the image data to the image viewer. In response to determining that the system capabilities of the client device do not satisfy the conditions for performing client-side rendering of the image data, the electronic processor is also configured to determine for the overlay data included in the medical image, whether the system capabilities of the client device satisfy conditions for performing client-side rendering of the overlay data. In response to determining that the system capabilities of the client device satisfy the conditions for performing client-side rendering of the overlay data, the electronic processor is configured to retrieve the overlay data and provide the overlay data to the image viewer application for client-side rendering of the overlay-data within the image viewer application. In response to determining that the system capabilities of the client device do not satisfy the conditions for performing client-side rendering of the overlay data, the electronic processor is further configured to provide a server-side rendered version of the overlay data to the image viewer. The medical image is displayed within the image viewer application.

Another embodiment provides a non-transitory computer-readable medium storing instructions that, when executed by an electronic processor, perform a set of functions. The set of functions include receiving user input selecting a medical image study for display within an image viewer application executed by a client device, the medical image study including a plurality of medical images and determining system capabilities of the client device. The set of functions also include determining for each of the plurality of medical images, whether the system capabilities of the client device and characteristics of the medical image satisfy conditions for performing client-side rendering of the medical image. In response to determining that the system capabilities of the client device and the characteristics of the medical image satisfy the conditions for performing client-side rendering of the medical image, the set of functions include retrieving raw medical image data corresponding to the medical image from an image repository and providing the raw medical image data corresponding to the medical image to the image viewer application executed by the client for client-side rendering of the medical image within the image viewer application. In response to determining that the system capabilities of the client device or the characteristics of the medical image do not satisfy the conditions for performing client-side rendering of the medical image, the set of functions include providing a server-side rendered version of the raw medical image data corresponding to the medical to the image viewer. A first set of the plurality of medical images is displayed within the image viewer application using the client-side rendering and a second set of the plurality of medical images is displayed within the image viewer application using server-side rendering Other aspects will become apparent by consideration of the detailed description and accompanying drawings and appendices.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
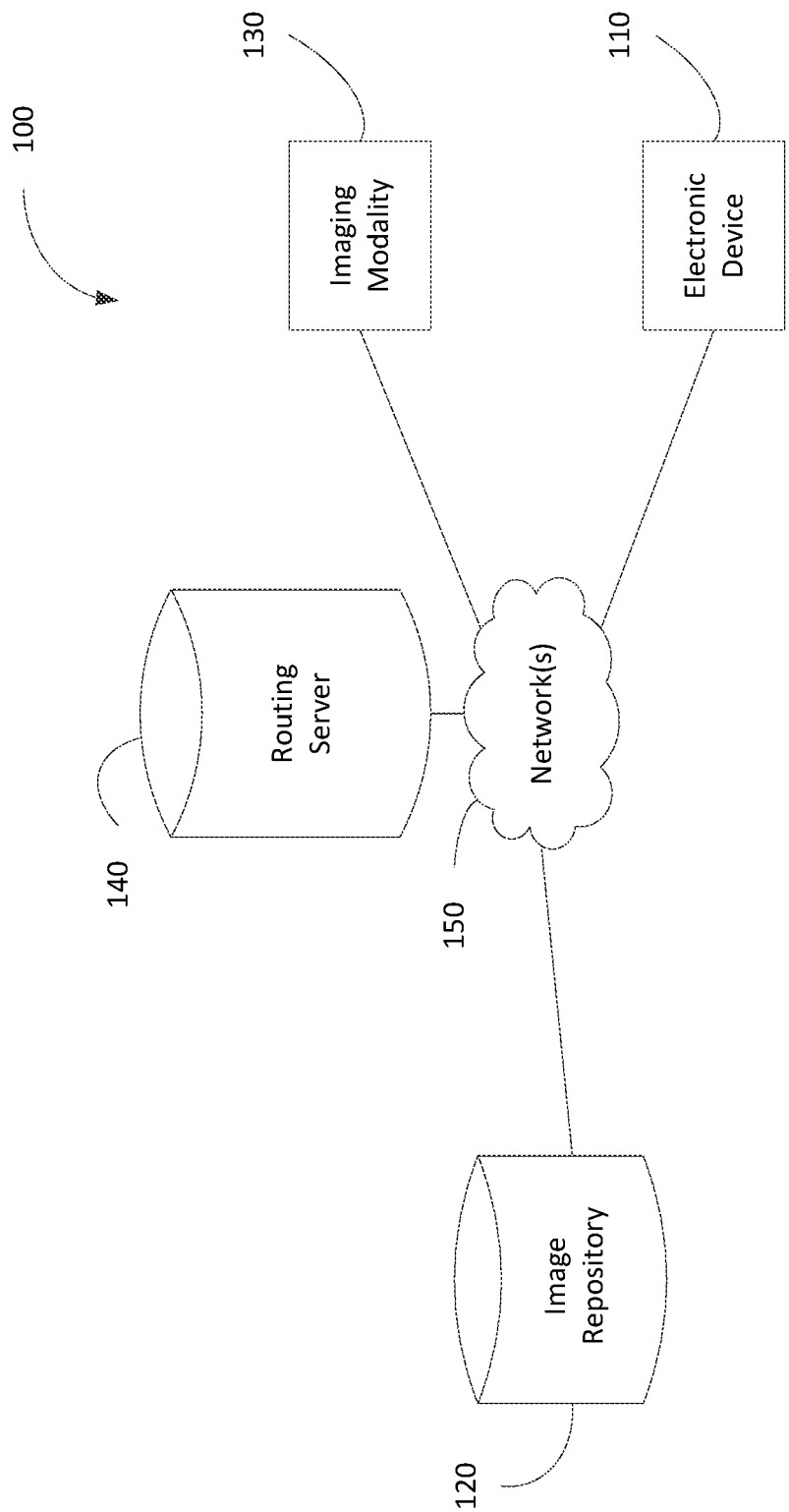
FIG. 1 schematically illustrates a system for displaying medical images on a client device according to some embodiments.

FIG. 1 illustrates a system 100 for displaying medical images on a client device 110. The client device 110 can include an electronic device associated with a recipient of a medical study, such as a radiologist or a physician reviewing or reading images generated during an imaging procedure. For example, the client device 110 may be a desktop computer, a terminal or workstation, a laptop computer, a tablet computer, a smart watch or other wearable, a smart telephone, and the like. The medical images are generally generated by an imaging modality 130, such as an X-Ray imaging system, a magnetic resonance imaging (MRI) system, a computed axial tomography (CAT) system, or the like. The medical images generated by the imaging modality 130 are routed and stored to an image repository 120. A routing server 140 controls access to the image repository 120 and, as described in more detail below, allows the client device 110 to access and view images stored in the image repository 120 over one or more wired or wireless networks 150, such as the Internet, a clinical messaging network, a local area network, or the like. In some embodiments, the system 100 includes additional components, such as multiple client devices 110, multiple image repositories 120, multiple routing servers 140, or the like. Also, in some embodiments, the routing server 140 may include the image repository 120.

The routing server 140 may be, for example, a picture archiving and communication system (PACS) server that serves as a gateway to the image repository 120. The routing server 140, the image repository 120, or both may be associated with a particular type or brand of imaging modality 130 or may be configured to handle images generated by a variety of types and brands of imaging modalities. Also, as noted above, in some embodiments, the image repository 120 is included in the routing server 140. In some embodiments, the routing server 140 also includes a web server that responds to requests received from one or more web browser applications. However, in other embodiments, a web server separate from the routing server 140 services these requests by acting as an intermediary device between the web browser applications and the routing server 140.

Figure 2:
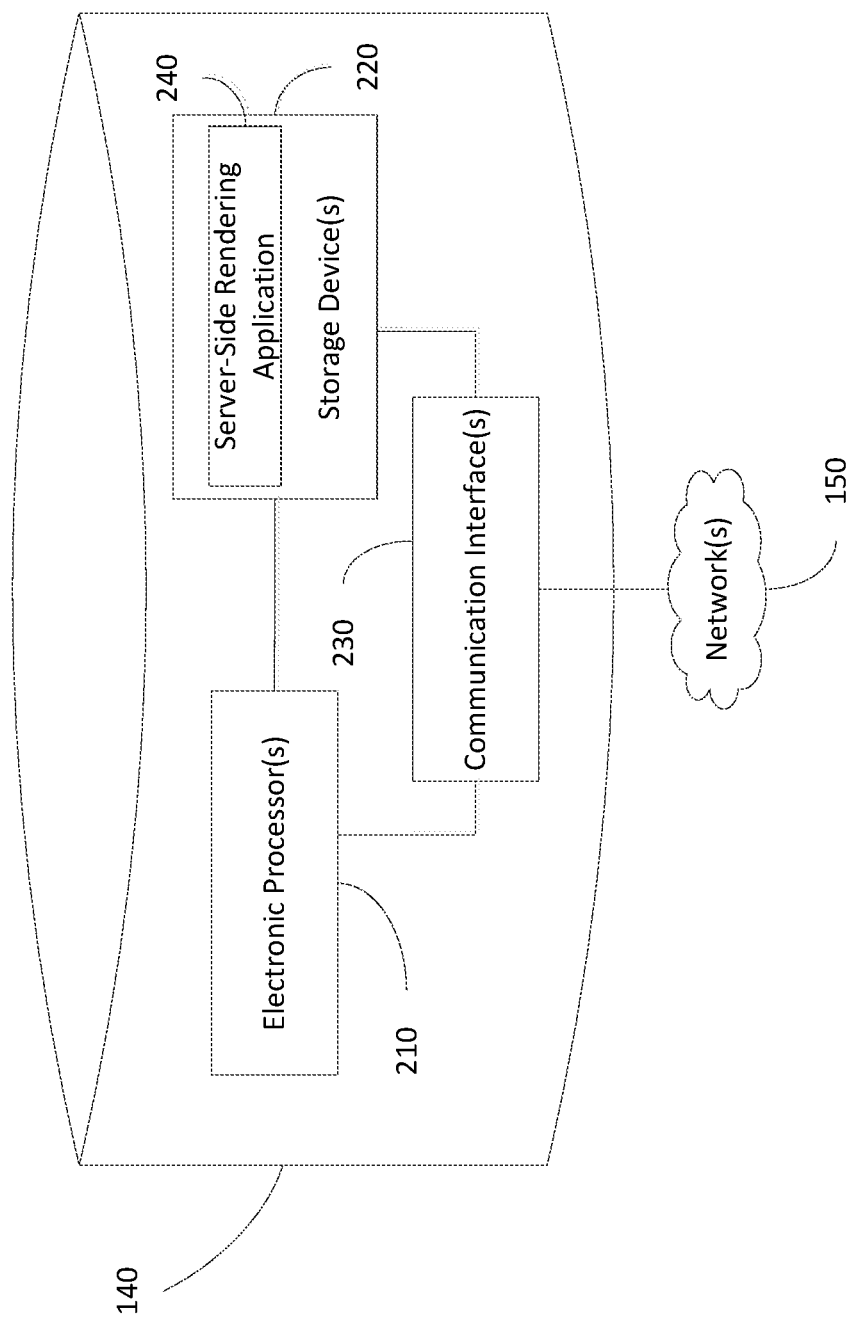
FIG. 2 schematically illustrates a routing server included in the system of FIG. 1 according to some embodiments.

As illustrated in FIG. 2, the routing server 140 includes one or more electronic processors 210, one or more computer-readable memory or storage devices 220, and one or more communication interfaces 230. The storage devices 220 include non-transitory memory, such as random access memory and/or read-only memory. The electronic processors 210 include a microprocessor or other electronic device configured to execute instructions stored in the storage devices 220. The storage devices 220 also store data used with and generated by execution of the instructions. The communication interfaces 230 allow the routing server 140 to communicate with external devices over the networks 150. The routing server 140 can use the networks 150 to communicate with the client device 110, the image repository 120, and the imaging modality 130 and, in some embodiments, uses different networks 150 to communicate with each device. However, in some embodiments, the routing server 140 is configured to have a dedicated interface or connection to one or more devices, such as the image repository 120.

The storage devices 220 included in the server 140 stores, among other things, a server-side rendering application 240. The server-side rendering application 240 converts raw medical image data stored in the image repository 120 into image formats viewable on an application executed by the client device 110. The raw medical image data includes raw pixel data generated by the imaging modality 130, such as, for example, data stored in the Neuroimaging Informatics Technology initiative (Nifti) format, Minc format, Digital Imaging and Communications in Medicine (DICOM) format, or the like. The server-side rendering application 240, when executed by the electronic processors 210, converts the raw pixel data into image formats, for example, JPEG, Tagged Image File Format (TIFF), Graphics Interchange Format (GIF), Bitmap (BMP), Portable Networks Graphic (PNG) format, Portable Document Format (PDF), or the like that are supported for viewing on the client device 110.

It should be understood that in some embodiments, the server 140 includes additional components than those illustrated in FIG. 2. It should also be understood that, in some embodiments, the functionality provided by the server 140 as described herein can be distributed among multiple servers, such as servers included in a cloud service or environment. In addition, it should be understood that although only a single client device 110 and a single imaging modality 130 are illustrated in FIG. 1, the routing server 140 can be configured to communicate with multiple different client devices 110, multiple different image repositories 120, and multiple different imaging modalities 130.

Figure 3:
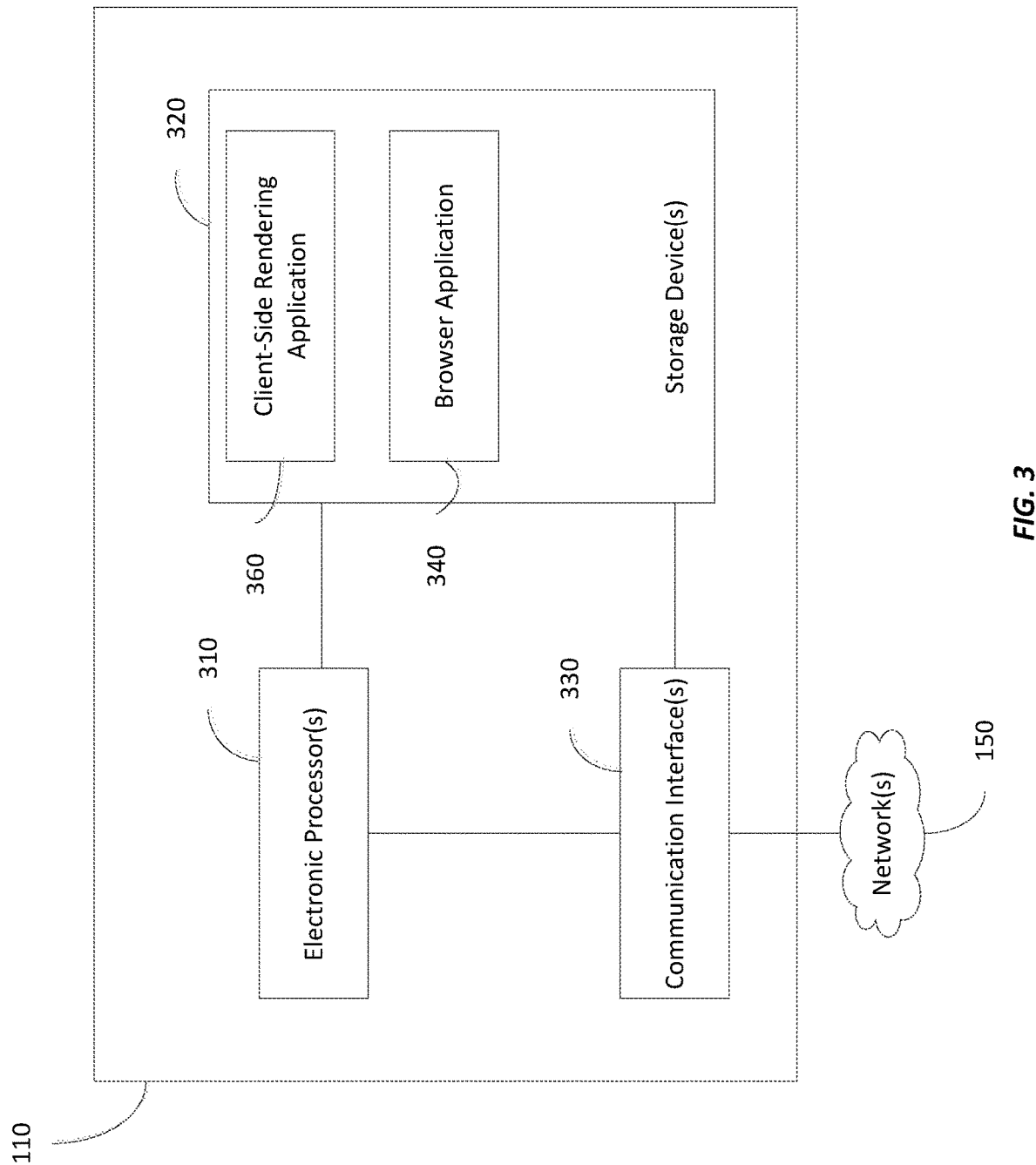
FIG. 3 schematically illustrates the client device included in the system of FIG. 1 according to some embodiments.

As illustrated in FIG. 3, the client device 110 includes similar components as the routing server 140. In particular, the client device 110 includes one or more electronic processors 310, one or more computer-readable storage devices 320, and one or more communication interfaces 330. The storage devices 320 include non-transitory memory, such as random access memory and/or read-only memory. The electronic processors 310 include a microprocessor or other electronic device configured to execute instructions stored in the storage devices 320. The storage devices 320 also store data used with and generated by execution of the instructions. The communication interfaces 330 allow the client device 110 to communicate with external devices over the networks 150. The client device 110 can use the networks 150 to communicate with the routing server 140. Although not illustrated in FIG. 3, the client device 110 may also include one or more human machine interfaces for receiving input from a user, providing output to a user, or a combination thereof. For example, the client device 110 may also include a keyboard, a mouse, an LCD display, an LED display, a touch screen display, or a combination thereof. It should be understood that in some embodiments, the client device 110 includes additional components than those illustrated in FIG. 3 or components in different configurations than those illustrated in FIG. 3.

The storage devices 320 included in the client device 110 stores, among other things, a browser application 340 and a client-side rendering application 360. The browser application 340 is, for example, Mozilla Firefox, Google Chrome, Internet Explorer, and the like. The browser application 340 receives a Uniform Resource Locater (URL) that directs the browser application 340 to a web server (for example, the routing server 140 or a separate intermediary web server as described above). The browser application 340 retrieves and renders, for example, a Hypertext Markup Language (HTML) markup and executes the contained JavaScript code.

The client-side rendering application 360 operates similar to the server-side rendering application 240. In particular, the client-side rendering application 360 receives raw medical image data and displays and modifies the raw medical image (zooming and the like) within the browser application 340 based on user input. In some embodiments, the client-side rendering application 360 also converts raw medical image data received from the image repository 120 (through the routing server 140) into image formats viewable within the browser application 340. The client-side rendering application 360 may be embedded in the browser application 340 or may be executed as an add-on to the browser application 340. Also, in some embodiments, the client device 110 stores and executes a dedicated viewer application in addition to or in place of the browser application 340. Accordingly, it should be understood that the mixed rendering functionality and the client-side rendering application 360 can be used with browser-based image viewers and dedicated viewer applications executed by the client device 110.

A user may access images in the image repository 120 by entering a URL associated with the routing server 140 in the browser application 340 executed by the client device 110. In some embodiments, the pages or user interfaces (UIs) accessible via the URL (as executed and rendered within the browser application 340) may prompt the user to enter the user's login credentials, a user identifier associated with the user, or other authenticating information. After any required authentication is complete, the user can access and view one or more images stored in the image repository 120. In some embodiments, the user may submit a request for specific images stored in the image repository. In addition or alternatively, images may be automatically downloaded separate from a specific user request for particular images. It should be understood that functionality described hereafter as being performed by the browser application 340 may be performed by the browser application 340 as stored and executed on the client device 110 through the execution of code (HTML and JavaScript code) received from the routing server 140 (or a separate web server).

Figure 4:
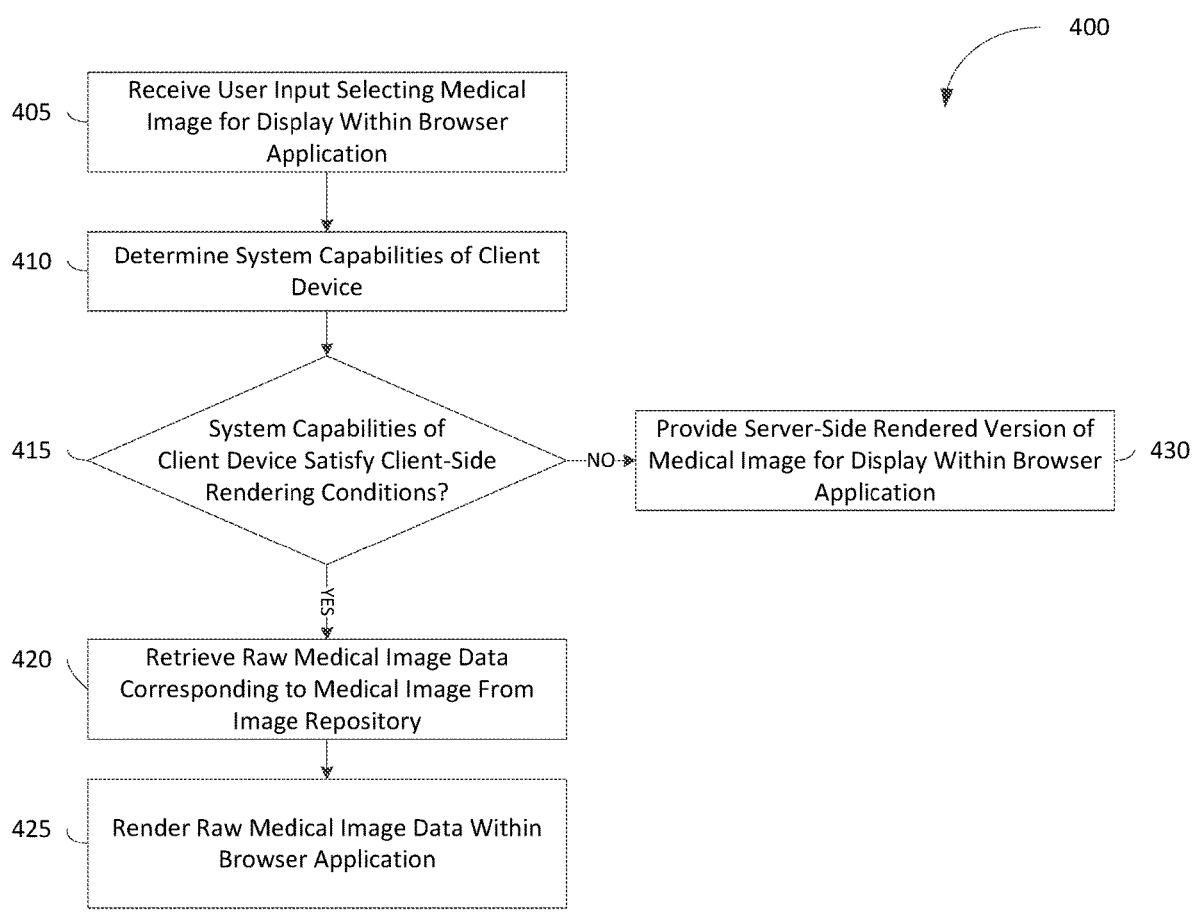
FIG. 4 is a flowchart illustrating a method for providing dynamic rendering of medical images performed by the system of FIG. 1 according to some embodiments.

FIG. 4 is a flowchart illustrating a method 400 for providing dynamic rendering of medical images performed by the system 100. The method 400 is described as being performed by the client device 110 (in particular, the electronic processors 310 executing instructions, including the browser application 340 and the client-side rendering application 360). However, the functionality described herein as being performed by the client device 110 (or a portion thereof) may be performed by the routing server 140. For example, as described below with respect to FIG. 4, the client device 110 may be configured to automatically determine whether to use client-side image rendering or server-side image rendering. However, the routing server 140 may similarly be configured to make this determination and transmit appropriate data to the client device 110. Similarly, the client device 110 and the routing server 140 may be configured to interact (exchange data) and work together to (i) determine system capabilities, (i) determine whether to perform client-side rendering, server-side rendering, or mixed rendering, or (ii) a combination thereof.

As illustrated in FIG. 4, the method 400 includes receiving user input selecting a medical image for display within the browser application 340 executed by client device 110 (at block 405). When a user logs in to the routing server 140 through the browser application 340, the browser application 340 may retrieve a worklist for the user. The worklist may include one or more medical studies that are assigned to or need to be reviewed by the user. Each medical study may include several medical images that were generated as part of the medical image study. Thus, a user may select a medical study or a medical image included in a particular study to view from a displayed worklist. It should be understood that although the method 400 is described with respect to a single medical image as one example, the method 400 may be similarly applied to set of images, such as a medical image study.

The method 400 also includes determining system capabilities of the client device 110 (at block 410). The system capabilities may include processing capabilities (speed, number of processors, types of processors, other types of hardware, or the like) of the client device 110 (the electronic processors 310), connection speed (for example, connection latency, connection bandwidth, or a combination thereof) or connection type (wired v. wireless, Wi-Fi vs. a local area network) between the client device 110 and the routing server 140, whether a dedicated image viewer (or a particular type of dedicated image viewer) is installed on the client device 110, the type of medical image selected (for example, a CAT scan, an MM image, or the like), or the like. In some embodiments, system capabilities of the client device 110 are determined dynamically when a user requests a particular medical image or a particular modification to a displayed image. In other embodiments, the system capabilities are dynamically determined in a predetermined frequency or in response to other triggering events. Dynamically determining the system capabilities allows the method 400 to react to changes in the system capabilities over time, including during or in between retrieval and display of an individual medical image.

The method 400 further includes dynamically determining whether the system capabilities of the client device 110 satisfy conditions for performing client-side image rendering (at block 415). The conditions for performing client-side image rendering may include one or more thresholds, metrics, ranges, or values for one or more of the system capabilities, such as a condition associated with one or more of a processing speed, a connection speed, particular types of dedicated image viewers, or the like. Also, in some embodiments, the conditions may include system capabilities of the routing server 140. For example, even when the system capabilities of the client device 110 satisfy one or more thresholds, metrics, ranges, values, or the like, the system capabilities may be compared with the system capabilities of the routing server 140 to determine whether rendering of the routing server 140 is faster or otherwise preferred. For example, in some embodiments, the client device 110 may satisfy minimum conditions for performing client-side image rendering, but the routing server 140 may still be able to perform the rendering faster or more efficiently and, thus, in this situation, the system capabilities of the client device 110 may not satisfy the conditions.

Depending on whether the system capabilities of the client device 110 satisfy the condition impacts whether a requested medical image should be provided via server-side rendering or client-side rendering. In particular, in response to determining that the system capabilities of the client device 110 satisfy the conditions for performing client-side imaging rendering, the method 400 includes retrieving raw medical image data corresponding to the medical image from the image repository 120 (at block 420) and providing the raw medical image data corresponding to the medical image to the browser application 340 executed by the client device 110 for client-side rendering of the medical image within the browser application 340 (at block 425). The client device 110 may execute the client-side rendering application 360 to display the received raw medical image data within the browser application 340.

Alternatively, in response to determining that the system capabilities of the client device 110 do not satisfy the conditions for performing client-side rendering of the medical image, the method 400 includes providing a server-side rendered version of the raw medical image data corresponding to the medical to the browser application 340 (at block 430).

The method 400 may similarly be used to re-render the medical image (re-determine system capabilities and re-determine whether the system capabilities satisfy the conditions) when a user subsequently requests a modification to the medical image (for example, changing the brightness contrast, or window level). Accordingly, in some embodiments, server-side rendering may initially be used to display a medical image at the client device 110 but as system capabilities of the client device 110 change, the medical image may be subsequently re-rendered using client-side rendering, which may improve subsequent speed and performance of the browser application 340.

It should be understood that in addition to considering system capabilities of the client device 110, the above method 400 may consider system capabilities of the routing server 140, the image repository, the networks 150, or a combination thereof. In addition, a user may be able to manually override the automatic determination of a type of rendering. Also, the method 400 may apply at least one rule that specify preferences for dynamically determining how to render a medical image within a viewer application executed by the client device 110 based on a particular user, group of users, the client device, the routing server 140, the image repository 120, a facility, a network, the browser application 340, the client-side rendering application 360, other image viewer applications installed on the client device, a patient, a time of day, or the like. These rules may be set by a user (or a system administrator). In addition or alternatively, these rules may be automatically set or modified using machine learning. For example, when a particular user (a particular radiologist) routinely selects client-side rendering for a particular type of imaging exam, a particular patient, or a particular client device 110, machine learning may be used to automatically set a rule for the user such that subsequent medical images are automatically rendered per the preference of the user.

In some embodiments, mixed rendering is also used. For example, portions of a particular medical image (or a particular medical study) may be better suited for client-side rendering while other portions of the medical image (or the medical study) may be better suited for server-side rendering. Thus, the functionality described above with respect to FIG. 4 can be applied to portions of an image study or a medical image to provide mixed rendering.

Figure 5:
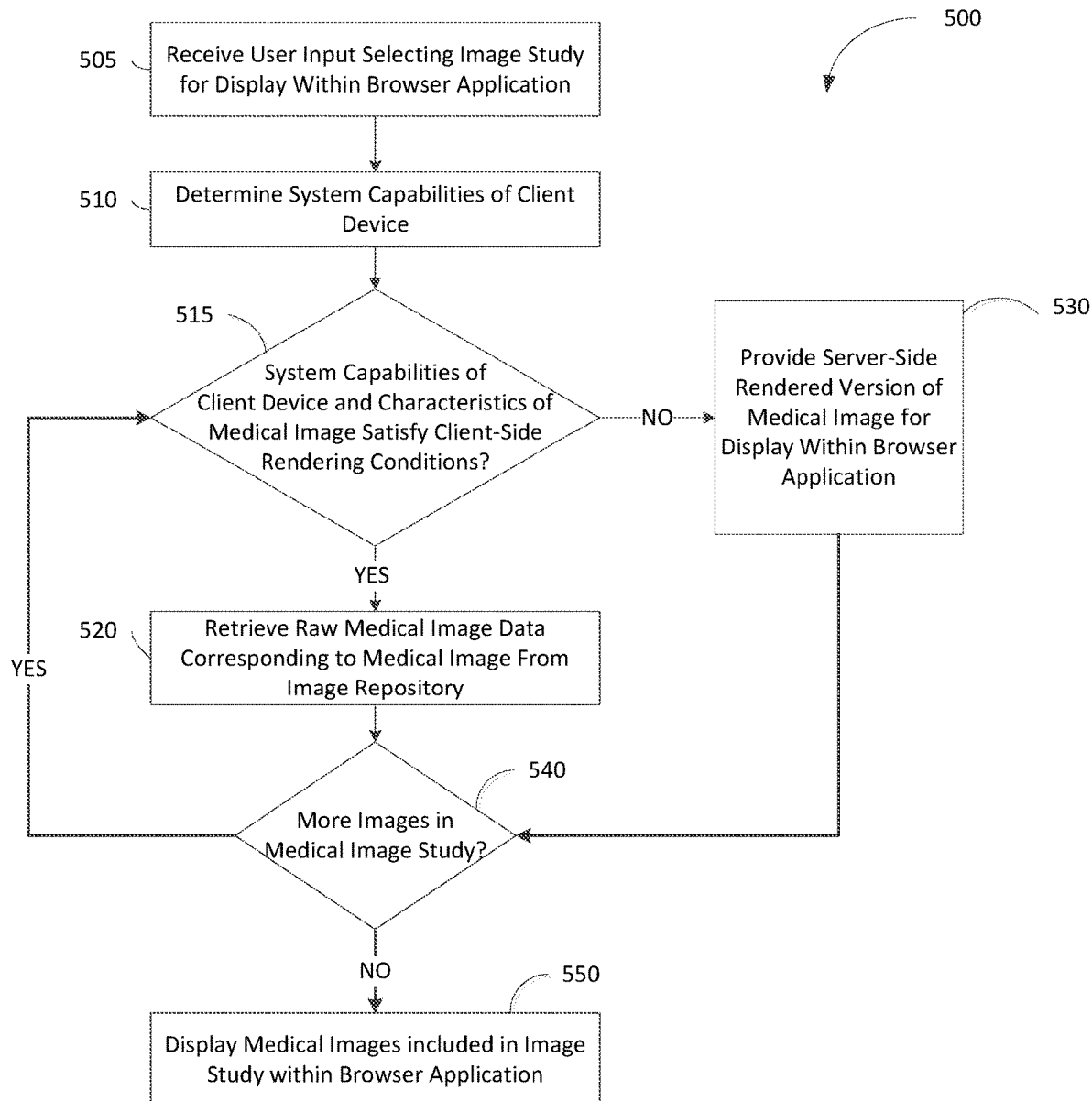
FIG. 5 is a flowchart illustrating a method for providing mixed rendering of medical images performed by the system of FIG. 1 according to some embodiments.

For example, FIG. 5 is a flowchart illustrating a method 500 for providing mixed rendering of medical images performed by the system 100. In some embodiments, the method 500 is directed to rendering some medical images in a medical image study using server-side rendering and the other medical images in the medical image study using client-side rendering. In other embodiments, the method 500 is directed to rendering a first portion of a medical image using server-side rendering and a second portion of the medical image using client-side rendering. For example, in some embodiments, an image itself could be rendered using server-side rendering and text and graphical overlays (for example, overlay data) for the image could be rendered using server-side rendering or client-side rendering based on the system capabilities of the client device 100. In some embodiments, when the client device 110 is capable of rendering the image itself, both the image and the text and graphical overlay are rendered by the client device. The method 500 is described as being performed by the client device 110 (in particular, the electronic processors 310 executing instructions, including the browser application 340 and the client-side rendering application 360). However, as noted above with respect to FIG. 4, in some embodiments, the routing server 140 (the electronic processors 210 executing instructions) may be configured to perform all or a portion of the functionality described below with respect to FIG. 5.

As illustrated in FIG. 5, the method 500 includes receiving user input selecting a medical image study for display within the browser application 340, wherein the medical image study includes a plurality of medical images (at block 505). As described above, a user may select an image study from a worklist.

The method 500 also includes determining system capabilities of client device 110 (at block 510) as described above with respect to FIG. 4. Based on the determined system capabilities, the browser application 340 assigns a first set of medical images included in the image study to be rendered on the server 140 and a second set of medical images included in the image study to be rendered on the client device 110. For example, for each medical image included in the image study, the system capabilities of the client device 110 and characteristics of the medical image are used to determine whether to use server-side rendering or client-side rendering (at block 515). For example, server-side rendering may be faster for certain image types (for example, MRI images) and client-side rendering may be faster for other image types (for example, CT scans). In one embodiment, the browser application 340 may assign a first portion of a medical image included in the image study to be rendered on the server 140 and a second portion of the medical to be rendered on the client device 110. For example, for each portion of the medical image, the system capabilities of the client device 110 are used to determine whether to use server-side rendering or client side-rendering. For example, as noted above, server-side rendering may be faster for rendering the actual image (that is, a first part) and client-side rendering may be faster for adding texts or graphical overlays (that is, a second part).

As described above with respect to FIG. 4, when client-side rendering conditions are satisfied for a particular medical image or for a first portion of a medical image included in the selected image study, the raw medical image data corresponding to the medical image or the data corresponding to the first portion of the medical image is retrieved from the image repository 120 (at block 520). Alternatively, in response to determining that the system capabilities of the client device 110, the medical image characteristics, or both do not satisfy the conditions for performing client-side rendering of the medical image or the first portion of the medical image included in the image study, the method 500 includes providing a server-side rendered version of the raw medical image data corresponding to the medical image or a second portion of the medical image to the browser application 340 (at block 530).

As illustrated in FIG. 5, this determination is repeated for each medical image included in the image study (at block 540). Medical images included in the medical image can then be displayed within the browser application 340, wherein some images or some portions of images may be displayed using server-side rendering and some images or some portions of images may be displayed using client-side rendering (such as by executing the client-side rendering application 360) (at block 550).

In some embodiments, the medical images rendered using server-side rendering may be displayed within a user interface that also displays medical images rendered using client-side rendering. Accordingly, the user interface may provide a seamless view of medical images wherein a user may be unaware of how each medical image was rendered. Also, as noted above, mixed rendering may be used for individual images included in an image study, portions of a medical image, or a combination thereof. For example, portions of a medical image may be provided via mixed rendering when system capabilities (connection speeds) change during rendering of an individual medical image.

Thus, embodiments described herein automatically and dynamically determine whether to provide a medical image using server-side rendering, client-side rendering, or mixed rendering, wherein a first portion of a medical image (or an image study) is provided using server-side rendering and a second portion of the medical image (or the image study) is provided using client-side rendering. Such automatic and dynamic processing improves computer performance and speed, clearly representing an improvement in computer-related technology. Furthermore, rules may be set (manually or automatically) and applied to customize rendering of medical images.

Various features and advantages of the invention are set forth in the following claims.

What is claimed is:

1. A method of displaying images on a client device, the method comprising:
    receiving user input selecting a medical image for display within an image viewer application executed by the client device;
    determining system capabilities of the client device;
    determining, with an electronic processor, whether the system capabilities of the client device satisfy conditions for performing client-side rendering of the medical image;
    in response to determining that the system capabilities of the client device satisfy the conditions for performing client-side rendering of the medical image
        retrieving raw medical image data corresponding to the medical image from an image repository, and
        providing the raw medical image data corresponding to the medical image to the image viewer application executed by the client for client-side rendering of the medical image within the image viewer application;
    in response to determining that the system capabilities of the client device do not satisfy the conditions for performing client-side rendering of the medical image, providing a server-side rendered version of the raw medical image data corresponding to the medical to the image viewer; and
    in response to receiving a modification to the medical image as displayed within the image viewer application, re-determining system capabilities of the client device and re-determining whether the system capabilities of the client device satisfy conditions for performing client-side re-rendering of the medical image based on the modification.

2. The method of claim 1, wherein determining the system capabilities of the client device includes determining at least one selected from a group consisting of a processing capability of the client device, a connection speed of the client device, and a connection type of the client device.

3. The method of claim 1, wherein determining whether the system capabilities of the client device satisfy conditions for performing client-side rendering of the medical image further comprises comparing the system capabilities of the client device with system capabilities of a server performing server-side rendering of the raw medical image data.

4. The method of claim 1, further comprising determining system capabilities of a routing server controlling access to the medical image and wherein determining whether the system capabilities of the client device satisfy the conditions for performing client-side rendering of the medical image includes determining whether the system capabilities of the client device and the system capability of the routing server satisfy the conditions for performing client-side rendering.

5. The method of claim 1, further comprising determining characteristics of the medical image and wherein determining whether the system capabilities of the client device satisfy the conditions for performing client-side rendering of the medical image includes determining whether the system capabilities of the client device and the characteristics of the medical image satisfy the conditions for performing client-side rendering.

6. The method of claim 1, wherein determining whether the system capabilities of the client device satisfy conditions for performing client-side rendering of the medical image includes comparing the system capabilities of the client device to at least one threshold associated with performing client-side rendering of the medical image.

7. The method of claim 1, wherein determining whether the system capabilities of the client device satisfy conditions for performing client-side rendering of the medical image includes comparing the system capabilities of the client device to at least one value associated with performing client-side rendering of the medical image.

8. The method of claim 1, wherein determining whether the system capabilities of the client device satisfy conditions for performing client-side rendering of the medical image includes comparing the system capabilities of the client device to at least one range associated with performing client-side rendering of the medical image.

9. Non-transitory computer-readable medium storing instructions that, when executed by an electronic processor, perform a set of functions, the set of functions comprising:
receiving user input selecting a medical image study for display within an image viewer application executed by a client device, the medical image study including a plurality of medical images;
determining system capabilities of the client device;
determining for each of the plurality of medical images, whether the system capabilities of the client device and characteristics of the medical image satisfy conditions for performing client-side rendering of the medical image;
in response to determining that the system capabilities of the client device and the characteristics of the medical image satisfy the conditions for performing client-side rendering of the medical image:
retrieving raw medical image data corresponding to the medical image from an image repository, and
providing the raw medical image data corresponding to the medical image to the image viewer application executed by the client for client-side rendering of the medical image within the image viewer application;
in response to determining that the system capabilities of the client device or the characteristics of the medical image do not satisfy the conditions for performing client-side rendering of the medical image, providing a server-side rendered version of the raw medical image data corresponding to the medical to the image viewer, and
in response to receiving a modification to the medical image as displayed within the image viewer application, re-determining system capabilities of the client device and re-determining whether the system capabilities of the client device satisfy conditions for performing client-side re-rendering of the medical image based on the modification,
wherein a first set of the plurality of medical images is displayed within the image viewer application using the client-side rendering and a second set of the plurality of medical images is displayed within the image viewer application using server-side rendering.

10. The computer-readable medium of claim 9, wherein determining the system capabilities of the client device includes determining at least one selected from a group consisting of processing capability of the client device, a connection speed of the client device, a connection type of the client device.

11. The computer-readable medium of claim 9, wherein determining whether the system capabilities of the client device and characteristics of the medical image satisfy conditions for performing client-side rendering includes comparing the system capabilities of the client device with system capabilities of a server performing server-side rendering of the raw medical image data.

12. The computer-readable medium of claim 9, the set of functions further comprising determining characteristics of the medical image and wherein determining whether the system capabilities of the client device satisfy the conditions for performing client-side rendering of the medical image includes determining whether the system capabilities of the client device and the characteristics of the medical image satisfy the conditions for performing client-side rendering.

13. The computer-readable medium of claim 9, wherein determining whether the system capabilities of the client device satisfy conditions for performing client-side rendering of the medical image includes comparing the system capabilities of the client device to at least one selected from a group consisting of a threshold, a value, and data range associated with performing client-side rendering of the medical image.

14. A system for displaying a medical image on a client device, the system comprising
an electronic processor configured to
receive user input selecting a medical image for display within an image viewer application executed by the client device, wherein the medical image includes image data and overlay data defining an overlay for the image data,
determine system capabilities of the client device,
determine for the image data included in the medical image, whether the system capabilities of the client device satisfy conditions for performing client-side rendering of the image data,
in response to determining that the system capabilities of the client device satisfy the conditions for performing client-side rendering of the image data, retrieve the image data and the overlay data and provide the image data and the overlay data to the image viewer application for client-side rendering of the image data and the overlay data within the image viewer application, in response to determining that the system capabilities of the client device do not satisfy the conditions for performing client-side rendering of the image data:

provide a server-side rendered version of the image data to the image viewer, determine for the overlay data included in the medical image, whether the system capabilities of the client device satisfy conditions for performing client-side rendering of the overlay data, in response to determining that the system capabilities of the client device satisfy the conditions for performing client-side rendering of the overlay data, retrieve the overlay data and provide the overlay data to the image viewer application for client-side rendering of the overlay-data within the image viewer application, and in response to determining that the system capabilities of the client device do not satisfy the conditions for performing client-side rendering of the overlay data, provide a server-side rendered version of the overlay data to the image viewer; and in response to receiving a modification to the medical image as displayed within the image viewer application, re-determining system capabilities of the client device and re-determining whether the system capabilities of the client device satisfy conditions for performing client-side re-rendering of the medical image based on the modification, wherein the medical image is displayed within the image viewer application.

15. The system of claim 14, wherein the electronic processor is included in the client device.

16. The system of claim 14, wherein the image viewer application is a browser application.

17. The system of claim 14, wherein the overlay data includes text overlay.

18. The system of claim 14, wherein the overlay data includes graphical overlay.

* * * * *